United States Patent
Li et al.

(10) Patent No.: US 11,319,522 B2
(45) Date of Patent: May 3, 2022

(54) PHOTOBIOREACTOR USED FOR ALGAE CULTIVATION, AND ALGAE CULTIVATION SYSTEM

(71) Applicant: Zhongzhi He, Hohhot (CN)

(72) Inventors: Bosheng Li, Beijing (CN); Hang Li, Beijing (CN)

(73) Assignee: Zhongzhi He, Inner Mongolia (CN)

( * ) Notice: Subject to any disclaimer, the term of this patent is extended or adjusted under 35 U.S.C. 154(b) by 842 days.

(21) Appl. No.: 15/575,282

(22) PCT Filed: May 18, 2016

(86) PCT No.: PCT/CN2016/082541
§ 371 (c)(1),
(2) Date: Apr. 27, 2018

(87) PCT Pub. No.: WO2016/184394
PCT Pub. Date: Nov. 24, 2016

(65) Prior Publication Data
US 2018/0223241 A1    Aug. 9, 2018

(30) Foreign Application Priority Data

May 19, 2015    (CN) .......................... 201510256337.3
May 19, 2015    (CN) .......................... 201510257777.0

(51) Int. Cl.
*C12M 1/00*    (2006.01)
*C12M 1/04*    (2006.01)
(Continued)

(52) U.S. Cl.
CPC ............. *C12M 41/12* (2013.01); *A01G 33/00* (2013.01); *C12M 1/04* (2013.01); *C12M 21/02* (2013.01);
(Continued)

(58) Field of Classification Search
CPC ......... A01G 33/00; C12M 21/02; C12M 1/04; C12M 23/02; C12M 29/14; C12M 31/10; C12M 41/12; C12M 41/48
(Continued)

(56) References Cited

U.S. PATENT DOCUMENTS

2009/0011492 A1* 1/2009 Berzin .................. C12M 31/02
435/257.1
2009/0023199 A1* 1/2009 Gal ........................ C12M 21/02
435/286.5
(Continued)

FOREIGN PATENT DOCUMENTS

CN    2257291    7/1997
CN    1213138 C  8/2005
(Continued)

OTHER PUBLICATIONS

Xue ,Shengchang et al "English machine translation of CN 203923169U document". Translated on Nov. 19, 2020.*

*Primary Examiner* — Liban M Hassan
(74) *Attorney, Agent, or Firm* — Umberg Zipser LLP; Jason Tejani

(57) ABSTRACT

The present application belongs to the technical field of biology. Provided is a photobioreactor used for algae cultivation, said photobioreactor comprising: a reactor main body, a separation unit, and a first aeration device. The reactor main body is a sealed irregular tubular shape, the separation unit is located within the reactor main body, and divides the reactor main body into two spaces, a left space and a right space, and the first aeration device is connected to a bottom portion of the reactor main body. Also provided is an algae cultivation system, comprising the photobioreactor, the second aeration device, and a temperature control system, and being capable of regulating the temperature of an algae solution.

17 Claims, 4 Drawing Sheets

(51) Int. Cl.
*C12M 1/34* (2006.01)
*A01G 33/00* (2006.01)
*C12M 1/36* (2006.01)

(52) U.S. Cl.
CPC .......... *C12M 23/02* (2013.01); *C12M 27/18* (2013.01); *C12M 29/14* (2013.01); *C12M 31/10* (2013.01); *C12M 41/48* (2013.01); *Y02A 40/80* (2018.01); *Y02P 60/20* (2015.11)

(58) Field of Classification Search
USPC ...................................... 435/292.1
See application file for complete search history.

(56) References Cited

U.S. PATENT DOCUMENTS

2010/0236135 A1* 9/2010 Kleinberger ........... C12M 23/00 44/307
2011/0318804 A1* 12/2011 Posten ................... C12M 31/08 435/168

FOREIGN PATENT DOCUMENTS

| | | | |
|---|---|---|---|
| CN | 1213139 C | | 8/2005 |
| CN | 1721523 | | 1/2006 |
| CN | 202265566 | | 6/2012 |
| CN | 203923169 U | * | 11/2014 |
| CN | 104928172 | | 9/2015 |
| CN | 104988059 | | 10/2015 |
| CN | 204737957 | | 11/2015 |
| CN | 204737963 | | 11/2015 |
| KR | 20130044599 A | * | 5/2013 |

* cited by examiner

PHOTOBIOREACTOR USED FOR ALGAE CULTIVATION, AND ALGAE CULTIVATION SYSTEM

TECHNICAL FIELD

The present invention relates to the field of biotechnology, particularly to a photobioreactor used for algae cultivation and an algae cultivation system.

BACKGROUND ART

Microalgae are a class of phytoplankton that grow widely in water and are generally smaller than 2 mm in size. Their cells act like sunshine-driven organic-producing factories that utilize light energy to absorb $CO_2$ and $H_2O$, and convert them into chemical energy such as carbohydrate, protein and fat and release $O_2$ through their efficient photosynthesis.

At present, a "highly efficient and large-scale culture technology for microalgae" is one of core microalgae biotechnologies. Microalgae photobioreactors have become a hotspot of research. There are different types of microalgae photobioreactors at home and abroad, and the shortcomings of the traditional raceway-culture method have been overcome to different extents. In short, the microalgae culture solution is introduced into the photobioreactor, and then inoculation is performed; the algae solution is stirred in a manner of gas-lift or flow-type gas exchange, mostly in enclosed photobioreactor. That is, the enclosed culture system is a photobioreactor made of transparent materials. In addition to light harvesting, this photobioreactor has many similarities to traditional photobioreactors for microbial fermentation in other respects. Enclosed photobioreactors can be used for unialgal culture and axenic culture of microalgae. Moreover, the cultivation conditions are easy to control, the cultivation density is high and the harvest is easy, so the efficiency is higher. However, the construction and operation costs are also increased.

For example, Chinese Patent No. ZL02134235.0 discloses an automated tubular photobioreactor for continuous production, in which the reaction vessel is a cylindrical communicating pipe of a transparent and light-transmitting material, the communicating pipe has an inlet end and an outlet end, and is connected with a mixing tank. The reactor is a three-dimensional tube formed by cross superposition of multiple layers of U-shaped communicating tube, the light source is located in the #-shaped three-dimensional space formed by cross superposition of the communicating tube. Although this kind of method and equipment for microalgae cultivation overcome the shortcomings of extensive cultivation of open ponds, the structure is complex, the large-scale equipment is difficult to implement, the construction cost is high, and the natural sunlight is hard to be fully utilized. Hence, such photobioreactor is not suitable for large scale cultivation of microalgae with low cost.

Chinese patent No. ZL03128138.9 discloses a closed tubular photobioreactor, which is composed of a three-dimensional double-row flat spiral tube and a unique U-shaped connecting elbow, twin columns, a zero shear force liquid delivery pump, a carbon dioxide injection device, a cold-heat exchanger and the like. The oxygen-discharge reaction column in the twin columns is provided with a negative pressure jet pump, which can effectively exclude the accumulated oxygen in the culture medium, and the control column can regulate the hydraulic pressure and automatically transport culture solution to the reaction tube by negative pressure. The reactor overcomes the shortcomings of the conventional reactor, such as large floor area and low efficiency, and can realize large-scale production. However, the structure is complex, and the manufacturing cost is high. Moreover, the reactor is positioned vertically, thus transporting culture solution and algae solution from the bottom to the top requires a lot of energy, the shearing force on the algal filament is greatly increased, and the cost for cultivating microalgae is also increased.

Chinese patent No. CN1721523A discloses a photobioreactor for large-scale culture of microalgae, which comprises a transparent tube, a gas desorbing device, an accessory pipe system, facilities that sense and control culture parameters and the like. The use of a large gas desorbing device and parallel connection of parallelly-arranged transparent tubes solve the problem of gas exchange in a closed tubular photobioreactor. However, there are also problems of high manufacturing cost and high operating cost.

Chinese patent No. ZL96216364.3 discloses a closed circulating shallow *Spirulina* cultivation device, which consists of an overflow ejector, an overflow plate photobioreactor, a reservoir, and a circulation pump connected in order, wherein the overflow plate photobioreactor made of light-transmitting materials is provided with multiple layers of baffled supporting plates that are arranged horizontally with overflow ports of the upper and lower layers in cross distribution. Although the reactor is very efficient, the structure of multiple layers of supporting plates is very complicated and not in favor of large-scale amplification.

Therefore, in view of the above shortcomings, it is necessary to provide a photobioreactor with the merits of high utilization rate of light energy, energy saving and low carbon, making full use of natural resources, high production efficiency of microalgae, and suitability for large-scale cultivation.

SUMMARY OF THE INVENTION (I) Technical Problems to be Solved

The technical problems to be solved by the present invention are inhibition of photosynthesis and low production efficiency of microalgae due to inability to timely release the oxygen generated by photosynthesis during the cultivation of microalgae as well as small natural lighting area, low utilization rate of the light energy, complicated existing production equipment, high energy consumption, high cost, and unsuitability for large-scale cultivation of algae.

(II) Technical Solutions

In order to solve the above technical problems, the present invention provides a photobioreactor for algae cultivation, comprising a reactor main body, a separation unit and a first aeration device, wherein the reactor main body has a bottom-sealed irregular tubular shape, and is made of a transparent material; the separation unit is located within the reactor main body, and divides the reactor main body into two spaces, left space and right space, and channels for connecting the left space and the right spaces are left at both the top and the bottom of the separation unit; and the first aeration device is connected with the bottom of either space of the reactor main body, and aerates upwards.

Wherein the cross section of the reactor main body has a shape of plum blossom with the same petals.

Wherein the separation unit is a transparent separator plate.

Wherein the separation unit is a transparent tube bank structure formed by connecting a row of vertical tubes in sequence, each of the vertical tubes is sealed at the upper end and the lower end, and a light source is disposed in a vertical tube at the middle position.

Wherein the vertical tubes at the edges of the transparent tube bank structure are long tubes, and the long tubes are closely contacted with the inner wall of the reactor main body; the vertical tubes at the middle position of the transparent tube bank structure are short tubes such that the channels for connecting the left space and the right space are formed at the top and the bottom of the transparent tube bank structure.

Wherein the length of the short tubes is shorter than the length of the long tubes by 10% to 40%; and the light source is a LED lamp.

Wherein the bottom of the reactor main body is provided with a liquid outlet, and the top is provided with a top cover with a liquid inlet.

Wherein the first aeration device comprises a gas source, a gas-guide pipe and a gas nozzle connected in sequence, and the gas-guide pipe extends downwardly from the top of the photobioreactor along the long tube to the bottom of the photobioreactor, and is connected with the gas nozzle.

Wherein the gas source consists of a wind-driven air compressor and a compressed air storage tank connected with each other, and the compressed air storage tank is connected to the gas-guide pipe.

Wherein the gas nozzle is a microporous gas disperser; and the reactor main body is provided with a metal base.

The present invention further provides an algae cultivation system, comprising an aeration pipe temperature control system, a second aeration device and an above-mentioned photobioreactor, wherein the photobioreactor is connected with the second aeration device via a gas-liquid heat exchanger immersed in a thermal-insulation water tank.

Wherein the aeration pipe temperature control system comprises a thermal-insulation water tank, a hot water generation unit, a cold water supply unit, a gas-liquid heat exchanger and a controller, the cold water supply unit, the hot water generation unit and the thermal-insulation water tank are sequentially connected; the gas-liquid heat exchanger is immersed in the thermal-insulation water tank, and has one end thereof connected with the second aeration device and the other end connected with the photobioreactor; the controller is connected with the cold water supply unit and the hot water generation unit to control cold water supply of the cold water supply unit and hot water generation of the hot water generation unit.

Wherein the hot water generating unit is a solar water heater, the installation position of the solar water heater is higher than that of the thermal-insulation water tank; a microporous gas disperser is provided at the bottom of the photobioreactor, the gas-liquid heat exchanger is connected with the microporous gas disperser.

Wherein the cold water supply unit comprises a cold water source and a cold water pump, the cold water source is connected with the solar water heater through the cold water pump, and the cold water pump is connected with a controller.

Wherein a temperature sensor is arranged in the thermal-insulation water tank, and the temperature sensor is connected with a controller.

Wherein the cold water source is a cold water tank, the thermal-insulation water tank and the cold water tank are arranged in a shape of rectangular ambulatory-plane (i.e, "回" shape) with the cold water tank located outside the thermal-insulation water tank, the height of the cold water tank is lower than the height of the thermal-insulation water tank, and the top of the thermal-insulation water tank is provided with an overflow channel which connects the thermal-insulation water tank and the cold water tank.

Wherein the second aeration device comprises a wind-driven compressor and a compressed gas storage tank connected with each other, wherein the compressed gas storage tank is connected with the gas-liquid heat exchanger.

Wherein a liquid inlet pipe network and a liquid outlet pipe network are further included. There are a plurality of photobioreactors, the inlet of each photobioreactor is connected with the liquid inlet pipe network, and the outlet of each photobioreactor is connected with the liquid outlet pipe network.

(III) Advantageous Effects

The photobioreactor and algae cultivation system for algae cultivation provided by the present invention has the following advantages:

1. The photobioreactor provided by the present invention divides the reactor main body into two spaces by the separation unit, and the aeration device is connected to the bottom of one space to aerate upwards. Since the specific gravity of the algae solution in this space is reduced due to the gas introduced, a difference in specific gravity is formed between the algae solutions in the two spaces. The algae solution in the aerated space travels to the top, passes through the channel left at the top of the two spaces, then travels downwards into the unaerated space as the liquid flows downwards, travels to the bottom, passes through the channel left at the bottom of the two spaces, and enters the aerated space as the liquid flows, thereby achieving four-dimensional circulating mixing of algae solution in upward, downward, forward and backward directions, which is different from the traditional gas-lift mixing, improves the mixing efficiency, increases the function of aeration, and reduces gas consumption. If the introduction of carbon dioxide-containing gas also increases the path and time for reaction and absorption of carbon, it creates an environment suitable for the growth of microalgae, and more importantly, it solves the problem that microalgae releases oxygen at any time in the process of cultivation by using the gas introduced. Hence, the compressed air introduced to the photobioreactor at least has the functions of mixing and stirring algae solution, supplying carbon source, controlling the temperature of algae solution, discharging oxygen at any time, and gas exchanging. The design of plum blossom-shaped irregular tube of the photobioreactor greatly increases the light energy utilization rate compared with the traditional circular tube design. Furthermore, by a wind-driven air compressor and the transparent tube bank structure with a built-in light source, wind energy and light energy are integrated into the photobioreactor system, achieving low-carbon and green microalgae cultivation with controllable microalgae cultivation conditions, high light utilization rate, and high density.

2. In the algae cultivation system provided by the present invention, under the control of the controller, the cold water supply unit supplies water for the hot water generation unit, the hot water generation unit generates hot water which is then introduced to the thermal-insulation water tank, the temperature sensor is placed in the thermal insulation water tank and capable of monitoring the water temperature in the thermal insulation water tank in real time, the thermal insulation water tank can maintain an appropriate water temperature and conducts heat exchange with the gas-liquid heat exchanger to transfer heat to the gas in the gas-liquid heat exchanger, and the gas-liquid heat exchanger is connected with the photobioreactor. Air or carbon dioxide-containing gas introduced to the photobioreactor can have a temperature beneficial to the growth of microalgae, and can provide an advantageous environment for the growth of microalgae after being introduced into the photobioreactor; the temperature sensor transmits the water temperature information of the thermal-insulation water tank to the controller, and the controller makes a judgment and controls the hot water generation unit and the cold water supply unit to work, thereby ensuring that the water temperature in the thermal-insulation water tank is in an appropriate state.

In the above figures, 1: a photobioreactor; 2: a thermal-insulation water tank; 3: a gas-liquid heat exchanger; 4: a cold water supply unit; 5: a hot water generation unit; 6: a temperature sensor; 7: a controller 8: a second aeration device; 10: a reactor main body; 11: a gas source; 101 an ultrasonic rod; 102: a transparent tube bank structure; 103: a separation unit; 104: a top cover; 105: a liquid inlet; 106: a first aeration device; 107: a liquid outlet; 108: a separation unit; 401: a cold water tank; 402: a cold water pump; 801: a compressed air storage tank; 802: a wind-driven air compressor; 1031: a long pipe; 1032: a short pipe; 1061: a gas-guide pipe; 1062: an gas nozzle.

SPECIFIC MODES FOR CARRYING OUT THE EMBODIMENTS

The specific embodiments of the present invention will be further described in details with reference to the figures and Examples below. The following examples are described for the purpose of illustrating the present invention rather than limiting the scope of the present invention.

Example 1

Figure 1:
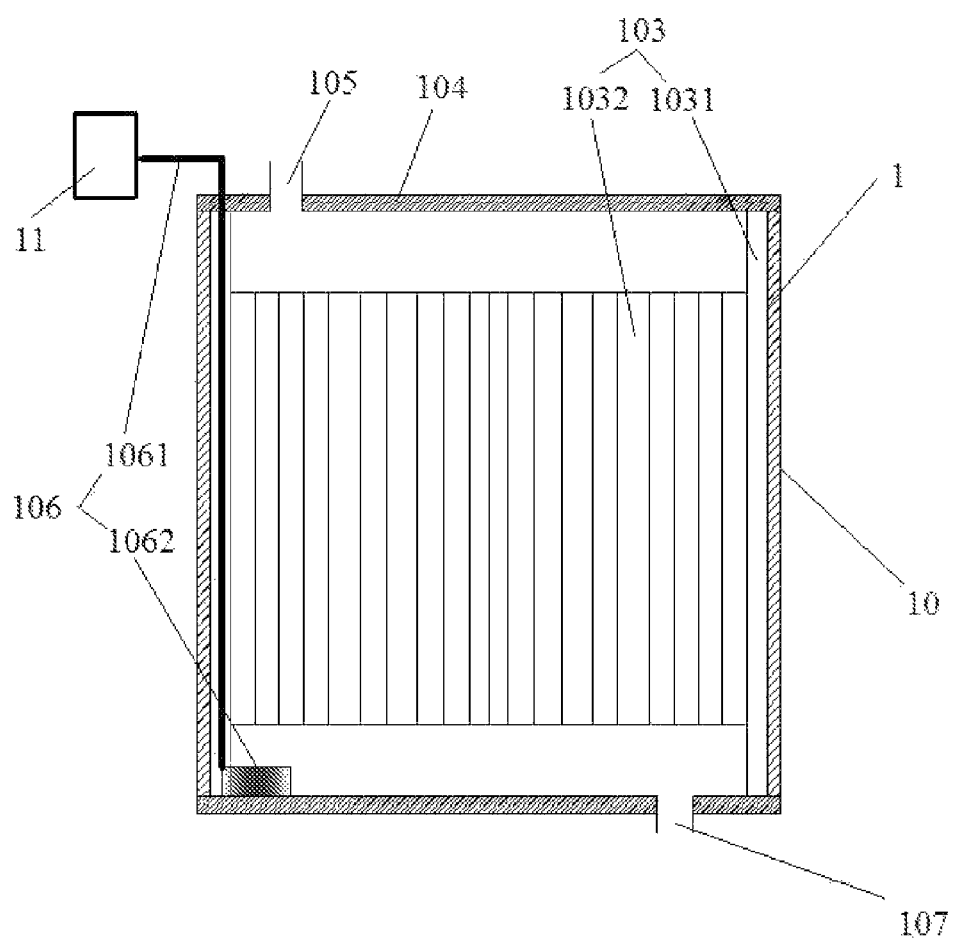
FIG. 1 is an overall structure diagram of the photobioreactor for algae cultivation according to Example 1 of the present invention.
Figure 2:
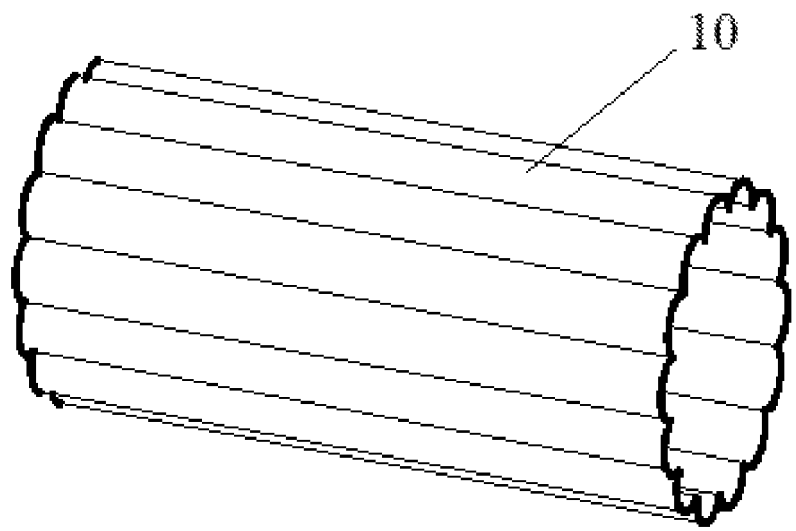
FIG. 2 is a stereogram of the reactor main body of the photobioreactor for algae cultivation according to Example 1 of the present invention.
Figure 3:
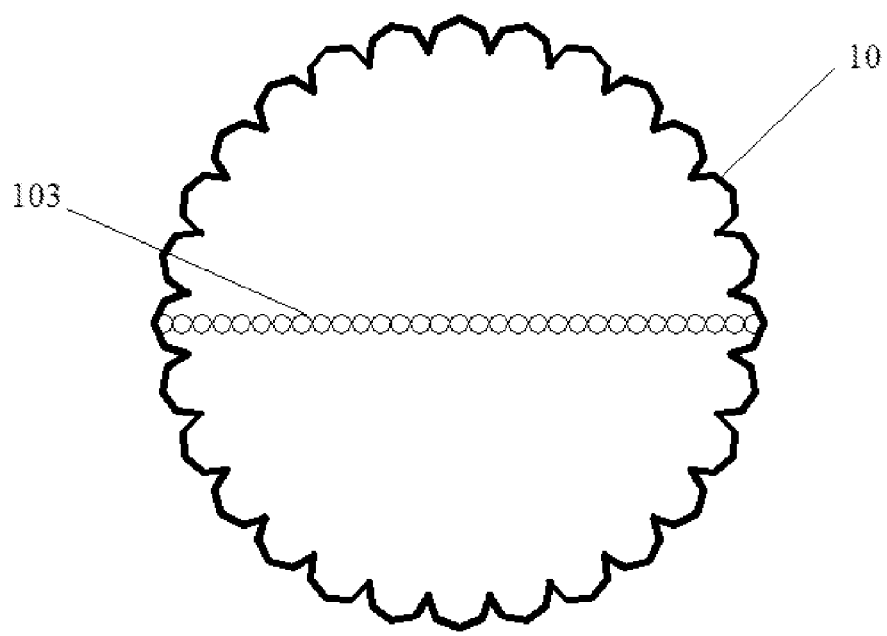
FIG. 3 is a cross-sectional view of the reactor of the photobioreactor for algae cultivation according to Example 1 of the present invention.

Specifically, as shown in FIG. 1 to FIG. 3, an example of the present invention provides a photobioreactor 1 for algae cultivation, which includes a reactor main body 10, a separation unit 103, and a first aeration device 106, wherein the reactor main body is a bottom-sealed tubular transparent body. As shown in FIG. 2 and FIG. 3, the cross section of the reactor main body 10 has a shape of plum blossom with the same petals, which greatly increases the illumination area and the light energy utilization rate by 50-70% relative to the traditional circular tube design. The gas-liquid heat exchanger is connected with the bottom of either space of the reactor main body 10.

Further, as shown in FIG. 1 and FIG. 3, the separation unit 103 is a transparent tube bank structure formed by connecting a row of vertical tubes in sequence, each of the vertical tubes is sealed at the upper end and the lower end, and a light source is disposed in the vertical tube at the middle position. The arrangement of the light source improves the lighting conditions inside the photobioreactor 1 in a cloudy day, thereby facilitating the growth of microalgae; an ultrasonic rod 101 for cleaning is arranged in the reactor main body 10, and connected with and controlled by the controller 7. The ultrasonic rod 101 is placed into the photobioreactor 1 after the reactor is filled with water so as to achieve automatic ultrasonic washing.

The above-mentioned separation unit 103 separates the reactor main body 10 into two spaces, and a first aeration device 106 is connected to the bottom of one space to aerate upwards. Since the specific gravity of the algae solution in this space is reduced due to the gas introduced, a difference in specific gravity is formed between the algae solutions in the two spaces. The algae solution in the aerated space travels to the top, passes through the channel left at the top of the two spaces, then travels downwards into the unaerated space as the liquid flows downwards, travels to the bottom, passes through the channel left at the bottom of the two spaces, and enters the aerated space as the liquid flows, thereby achieving four-dimensional circulating mixing of the algae solution in upward, downward, forward and backward directions, which is different from the traditional gas-lift mixing, improves the mixing efficiency, increases the function of aeration, and reduces gas consumption.

Typically, the bottom of the reactor main body 10 is provided with a liquid outlet 107. The cultivated algae liquid can flow out through the liquid outlet to enter the next step. The top of the reactor main body 10 is provided with a top cover 104 with a liquid inlet 105 to prevent other matters from falling into the reactor main body 10 which matters may cause pollution as the algae solution flows; a metal base can be provided for the reactor main body 10 in use, and the reactor is placed on the metal base. The first aeration device 106 includes a gas source 11, a gas-guide pipe 1061 and a gas nozzle 1062 connected in sequence. Further, the gas source 11 is an air compressor and a compressed air storage tank connected with each other. The compressed air storage tank is connected with the gas-guide pipe 1061 which extends from the top to the bottom of the reactor main body 10 and is connected with the gas nozzle 1062. A microporous gas disperser can be selected as the gas nozzle 1062 to aerate continuously and uniformly upwards. The compressed air storage tank can be used to store gas.

As shown in FIG. 1 and FIG. 3, the vertical tubes at the edges of the transparent tube bank structure are long tubes 1031, and the long tubes 1031 are closely contacted with the inner wall of the reactor main body 10. The inside of the long tubes may or may not be provided with a light source, because the position adjacent to the edge correspondingly has a natural lighting environment. A gas-guide pipe extends downwards from the top of the photobioreactor 1 along the long tube to the bottom of the photobioreactor 1, and is connected with gas nozzle 1062. The vertical tubes at the middle position of the transparent tube bank structure are short tubes 1032 such that the channels for connecting the left space and the right space are formed at the top and the bottom of the transparent tube bank structure. The length of the short tubes 1032 is shorter than the length of the long tubes 1031 by 10% to 40%; and the light source is a LED lamp.

Since the introduced gas leads to the difference in specific gravity between the algae solutions in the front and rear spaces, the algae solution of the aerated space travels to the top and enters into the other space and travels downwards as the liquid flows downwards, which greatly increases the mixing efficiency and reduces the gas consumption. If the introduction of carbon dioxide-containing gas also increases the path and time for reaction and absorption of carbon, more importantly, it solves the problems of temperature control and oxygen release at any time in the process of cultivation by using the gas introduced.

Figure 4:
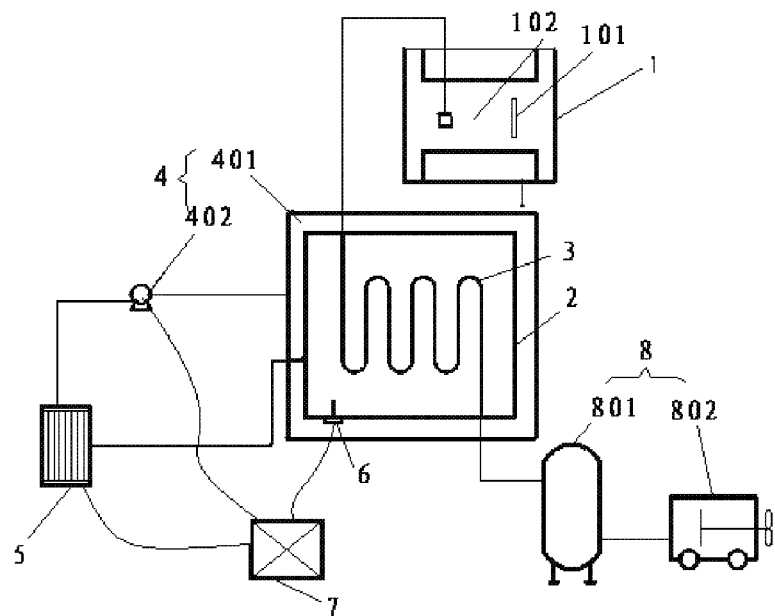
FIG. 4 is a schematic diagram of the algae cultivation system according to Example 1 of the present invention.

As shown in FIG. 4, the algae cultivation system provided in another aspect of the present invention includes an aeration pipe temperature control system, a second aeration device 8, and the above-mentioned photobioreactor 1. The photobioreactor 1 is connected with the second aeration device 8 via a gas-liquid heat exchanger 3 immersed in a thermal-insulation water tank 2. The second aeration device 8 preferably consists of a wind-driven air compressor 802 and a compressed air storage tank 801 connected with each other, and the compressed air storage tank 801 is connected to the gas-liquid heat exchanger 3, so that wind energy can be utilized effectively through the wind-driven compressor while gas source supply is realized, and low-carbon and green cultivation is achieved.

The photobioreactor 1 is provided with a transparent tube bank structure 102 in the center and a light source is arranged in the vertical pipe at the middle position of the transparent tube bank structure 102, such that algae solution can be circulated smoothly (four-dimensional circulating mixing) and light can be supplemented in circular tube. The illuminant is isolated from the algae solution, and good lighting conditions are provided.

The aeration pipe temperature control system includes a thermal-insulation water tank 2, a hot water generation unit 5, a cold water supply unit 4, a gas-liquid heat exchanger, a controller 7 and a temperature sensor 6. The cold water supply unit 4, the hot water generation unit 5 and the thermal-insulation water tank 2 are connected in sequence; one end of the gas-liquid heat exchanger is connected with the second aeration device, and the other end is connected with the photobioreactor. The gas-liquid heat exchanger 3 between the photobioreactor 1 and the second aeration device 8 is immersed in the thermal-insulation water tank 2 to allow balance of gas-liquid heat exchange. The temperature sensor 6 is arranged in the thermal-insulation water tank 2 and is connected with the controller 7, the hot water generation unit 5 and the cold water supply unit 4 are electrically connected with the controller 7, and are respectively controlled by the controller.

In the above embodiment, under the control of the controller, the cold water supply unit supplies water for the hot water generation unit, the hot water generation unit generates hot water which is then introduced to the thermal-insulation water tank, and the temperature sensor 6 is placed in the thermal-insulation water tank 2 to monitor the water temperature of the thermal-insulation water tank 2 in real time. The thermal-insulation water tank 2 is kept at an appropriate water temperature so as to conduct heat exchange with the gas-liquid heat exchanger 3. Heat is transferred to the gas in the gas-liquid heat exchanger 3 connected with the photobioreactor, and air or carbon dioxide gas introduced to the photobioreactor can have a temperature facilitating the growth of microalgae, and can provide an environment beneficial to the growth of microalgae after being introduced to the photobioreactor 1; the temperature sensor 6 transmits the water temperature information of the thermal-insulation water tank 2 to the controller 7, and the controller 7 makes a judgment and controls the hot water generation unit 5 and the cold water supply unit 4 to work, thereby ensuring that the water temperature in the thermal-insulation water tank 2 is in an appropriate state.

Specifically, the hot water generation unit 5 is a solar water heater which is connected with the thermal-insulation water tank 2 to provide hot water to the thermal-insulation water tank 2. The bottom of the photobioreactor is provided with a microporous gas disperser, the gas-liquid heat exchanger is connected with the microporous gas disperser. Air or carbon dioxide introduced to the photobioreactor is dispersed by the microporous gas disperser, and can be uniformly introduced into the algae solution, which is beneficial to well mixing with the algae solution and thereby beneficial to the growth of algae. Specifically, the cold water supply unit 4 includes a cold water source and a cold water pump 402, and specifically, the cold water source is a cold water tank 401 which is connected with a solar water heater through the cold water pump 402.

The cold water source (tank) is connected with the water inlet pipe of the solar water heater through the cold water pump. The controller and the temperature sensor monitor the water temperature change in the water heater. When setting temperature is reached, the cold water pump starts to transfer the hot water at the setting temperature to the thermal-insulation water tank, at this time the water heater is filled with cold water to be heated. In this way, the thermal-insulation water tank can be continuously and periodically provided with hot water at the setting temperature, thereby achieving the purposes of controlling water temperature, controlling the temperature of the compressed air in the heat exchanger, and controlling the temperature of the photobioreactor. By supplying the hot water source with a solar water heater, solar energy, a clean energy source, is utilized, which is low carbon and environment-friendly.

Preferably, the thermal-insulation water tank 2 and the cold water tank 401 are designed to be adjacent to each other or in a shape of rectangular ambulatory-plane with the thermal-insulation water tank inside and the cold water tank at the periphery. In general, the cold water tank has a height less than that of the thermal-insulation water tank, the top of the thermal-insulation water tank is provided with an overflow channel (overflow port) that connects the thermal-insulation water tank with the cold water tank. When the hot water exceeds the volume of the thermal-insulation water tank, the hot water automatically flows into the cold water tank through the overflow port. This design reduces heat loss and maintains the temperature of the thermal-insulation water tank to the utmost extent, and allows more convenient temperature control of the thermal-insulation water tank.

Further, the algae cultivation system comprises a liquid inlet pipe network, a liquid outlet pipe network and a plurality of photobioreactors 1. The liquid inlet of each photobioreactor 1 is connected with the liquid inlet pipe network, and the liquid outlet of each photobioreactor 1 is connected with the liquid outlet pipe network. In this way, large-scale microalgae cultivation can be improved by arrangement of the liquid inlet pipe network, the liquid outlet pipe network and the plurality of photobioreactors 1.

In this example, solar energy and wind energy are integrated into the algae cultivation system, utilizing clean energy source (which can provide 95-99% of the energy source) as the energy source in the microalgae cultivation process is achieved, and green low-carbon cultivation is realized; the temperature and other cultivation conditions in the algae cultivation system can be controlled by the controller 7 (usually a computer) so as to achieve the purpose of high and stable yield; and accumulation of one or some bioactive substances in the microalgae cells can also be achieved by controlling the cultivation conditions.

Example 2

Figure 5:
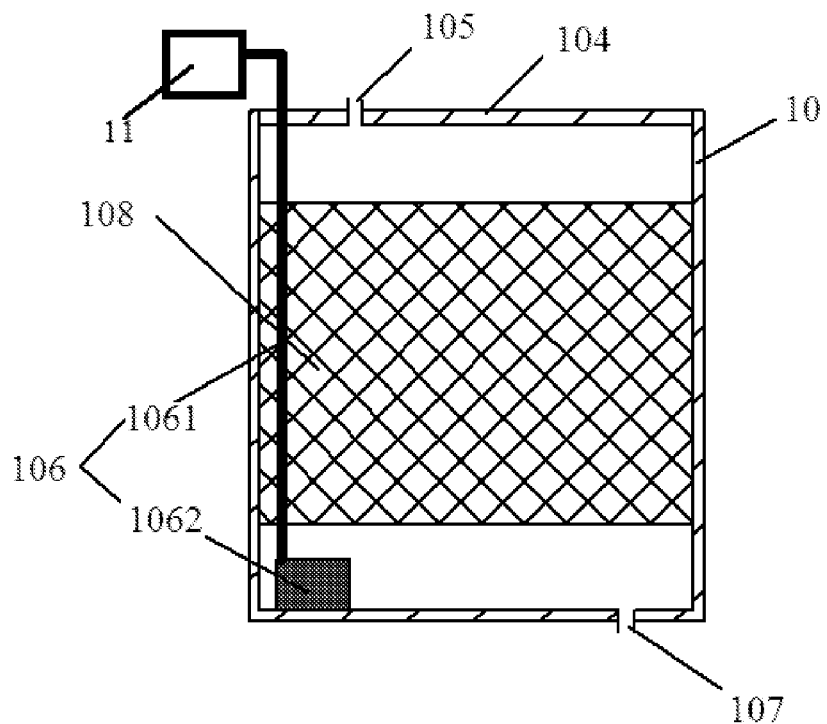
FIG. 5 is an overall structure diagram of the photobioreactor for algae cultivation according to Example 2 of the present invention.
Figure 6:
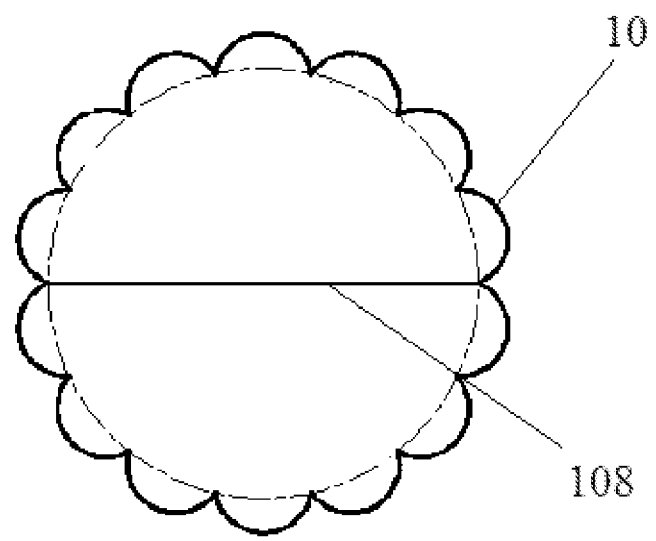
FIG. 6 is a cross-sectional view of the reactor of the photobioreactor for algae cultivation according to Example 2 of the present invention.

As shown in FIG. 5 and FIG. 6, this example is basically the same as Example 1, and the similarities are not described again, and the difference lies in that the separation unit 108 of the present example is a transparent separator plate and is located inside the reactor main body 10. The reactor main body 10 is divided into two spaces by the separation unit 108. Channels for connecting the left and the right spaces are left at the top and the bottom of the transparent separator plate. The separator plate is transparent and does not affect lighting.

The photobioreactor for algae cultivation and the algae cultivation system provided in the examples of the present invention have the following advantages:

(1) In the photobioreactor provided in the examples of the present invention, the reactor main body is divided into two spaces by a separation unit, and the bottom of one space is connected with a first aeration device to aerate upward, and algae solution containing a large amount of microbubbles is formed in this space and travels upward. The algae solution in the aerated space travels to the top, passes through the channel left at the top of the two spaces, travels downwards into the other space without aeration as the liquid flows downwards, then travels to the bottom, passes through the channel left at the bottom of the two spaces, and enters the aerated space as the liquid flows. In this way, liquid supplements downwards continuously to form a circulating state of the algae solution so as to achieve the effect of uniformly mixing algal filaments, discharging oxygen gas, controlling the temperature of the algae solution and eliminating the gradient of nutrient, illumination and temperature in the reactor.

(2) Under the control of the controller, the cold water supply unit supplies water to the hot water generation unit, the hot water generation unit generates hot water which is introduced to the thermal-insulation water tank, and the temperature sensor is placed in the thermal-insulation water tank to monitor the water temperature of the thermal-insulation water tank in real time. The thermal-insulation water tank is kept at an appropriate water temperature so as to conduct heat exchange with the gas-liquid heat exchanger. Heat is transferred to the gas in the gas-liquid heat exchanger connected with the photobioreactor, and air or carbon dioxide gas introduced to the photobioreactor can have a temperature facilitating the growth of microalgae, and can provide an environment beneficial to the growth of microalgae after being introduced into the photobioreactor; the temperature sensor transmits the water temperature information of the thermal-insulation water tank to the controller, and the controller makes a judgment and controls the hot water generation unit and the cold water supply unit to work, thereby ensuring that the water temperature in the thermal-insulation water tank is in an appropriate state.

(3) The thermal-insulation water tank and the cold water tank are designed to be adjacent to each other or in a shape of rectangular ambulatory-plane, which serves multiple purposes: ① the temperature of hot water in the thermal-insulation water tank can be corrected in time; ② the excessive heat is transferred to the cold water tank timely to reduce heat dissipation and increase water temperature of the cold water tank, so that the heating time of the water heater is shortened and energy is saved; ③ the installation position of the solar water heater is higher than that of the thermal-insulation water tank; the height difference between the solar water heater and the thermal-insulation water tank and the height difference between the thermal-insulation water tank and the cold water tank are utilized to achieve automatic flow and overflow, which is energy saving and highly efficient; and ④ this design is clever and simple, and easy to achieve large-scale production. In the present invention, the photobioreactor is provided with compressed air at a setting temperature ($CO_2$ gas can also be mixed at a certain concentration) to reach multiple purposes, namely to realize sufficient mixing of the algae solution, to realize gas exchange and the oxygen discharge of living cells at any time, to realize temperature control of the algae solution, and to provide a carbon source for microalgae. Here, the heat energy comes from solar energy, the energy for compressing air comes from wind energy, and the $CO_2$ gas comes from the exhaust gas which is discharged from factories and pretreated. Therefore, this system makes full use of natural resources to provide an environment suitable for the growth of microalgae, and it may be said that the whole cultivation system uses clean energy and is low-carbon, green, environment-friendly and easy to realize automatic control. By the design of each photobioreactor being connected with the liquid inlet pipe network and the liquid outlet pipe network, the present invention has the advantages of simple structure, flexible assembly and controllable algae cultivation conditions, clean and low-carbon property, environmental friendliness, stable quality, high yield, low cost operation and large-scale production.

(4) By using the solar water heater and the wind-driven air compressor 802, light energy and wind energy are introduced into the photobioreactor system and the algae cultivation system to minimize the energy consumption of microalgae cultivation and to realize green, low-carbon and environment-friendly cultivation. Arrangement of the liquid inlet pipe network, the liquid outlet pipe network and multiple photobioreactors 1 can expand the production scale of the algae cultivation system of the present invention, increase production efficiency and reduce production cost.

The foregoing examples are merely preferred examples of the present invention and are not used to limit the present invention. Any modifications, equivalent substitutions, improvements, and the like made within the spirit and principle of the present invention should be included in the protection scope of the present invention.

INDUSTRIAL PRACTICABILITY

The present invention provides a photobioreactor for algae cultivation and an algae cultivation system, wherein the photobioreactor for algae cultivation comprises: a reactor main body, a separation unit, and an aeration device, wherein the reactor main body has a bottom-sealed tubular shape, and is made of a transparent material; the separation unit is located within the reactor main body, and divides the reactor main body into two spaces, left space and right space, and channels for connecting the left space and the right space are left at both the top and the bottom of the separation unit; and the aeration device is connected with the bottom of either space of the reactor main body, and aerates upwards. The present invention provides an algae cultivation system constructed by the photobioreactor, comprising an aeration pipe temperature control system, an aeration device and the above-mentioned photobioreactor, wherein the photobioreactor is connected with the aeration device via a gas-liquid heat exchanger immersed in a thermal-insulation water tank. The reactor main body is divided into two spaces by a separation unit, and the bottom of one space is connected with an aeration device to aerate upwards, and the algae solution containing a large amount of microbubbles is formed in this space and travels upwards. The algae solution in the aerated space travels to the top, passes through the channel left at the top of the two spaces, travels downwards to the other space without aeriation as the liquid flows downwards, then travels to the bottom, passes through the channel left at the bottom of the two spaces, and enters the aerated space as the liquid flows. In this way, liquid supplements downwards continuously to achieve a circulating state of the algae solution so as to achieve the effect of uniformly mixing algal filaments, discharging oxygen gas, controlling the temperature of the algae solution and eliminating the gradient of nutrient, illumination and temperature in the reactor. The present invention has strong practical applicability.

What is claimed is:

1. A photobioreactor used for algae cultivation, comprising a reactor main body, a separation unit and a first aeration device, wherein the reactor main body has a generally vertically oriented bottom-sealed tubular shape and is made of a transparent material; the separation unit is located within the reactor main body and divides the reactor main body into two spaces, a left space and a right space, the separation unit has a height that is shorter than a height of the reactor main body, the separation unit is attached to the reactor main body above a bottom thereof and below a top thereof for fluidly connecting the left space and the right space of the reactor main body above and below of the separation unit; wherein the first aeration device is connected with a bottom of one of the left space or the right space of the reactor main body, wherein the first aeration device comprises a gas source and a gas nozzle in fluid communication with the gas source, and wherein the gas dispenser aerates upwards, whereby causing a circulation of the algae solution: first, upwards in one of the left space or the right space containing the first aeration device, then moving above the separation unit to the other one of the left space or the right space, then moving down towards the bottom of the reactor main body, and finally moving below the separation unit back to the one of the left or the right space containing the first aeration device, and wherein the reactor main body has a scalloped cross-sectional shape of a plum blossom with same petals, whereby increasing illumination area and light energy utilization rate by at least 50% as compared to a circular cross-sectional shape with the same diameter.

2. The photobioreactor according to claim 1, wherein the separation unit is a transparent separator plate.

3. The photobioreactor according to claim 1, wherein the separation unit is a transparent tube bank structure formed by connecting a row of vertical tubes in sequence, each of the vertical tubes is sealed at the upper end and the lower end, and a light source is disposed in a vertical tube at the middle position.

4. The photobioreactor according to claim 3, wherein the vertical tubes at the edges of the transparent tube bank structure are a plurality of first tubes having a first length, and the plurality of first tubes are closely contacted with the inner wall of the reactor main body; the vertical tubes at the middle position of the transparent tube bank structure are a plurality of second tubes having a second length such that channels for connecting the left space and the right space are formed at the top and the bottom of the transparent tube bank structure, wherein the first length is greater than the second length.

5. The photobioreactor according to claim 4, wherein the second length is shorter than the first length by 10% to 40%; and the light source is a LED lamp.

6. The photobioreactor according to claim 1, wherein the bottom of the reactor main body is provided with a liquid outlet, and the top is provided with a top cover with a liquid inlet.

7. The photobioreactor according to claim 4, wherein the first aeration device further comprises a gas-guide pipe with the gas source, the gas-guide pipe, and the gas nozzle connected in sequence, and the gas-guide pipe extends downwards from the top of reactor along one of the plurality of first tubes to the bottom of the reactor, and is connected with the gas nozzle.

8. The photobioreactor according to claim 7, wherein the gas source consists of a wind-driven air compressor and a compressed air storage tank connected with each other, and the compressed air storage tank is connected to the gas-guide pipe.

9. The photobioreactor according to claim 7, wherein the gas nozzle is a microporous gas disperser; and the reactor main body is provided with a metal base.

10. An algae cultivation system, comprising: an aeration pipe temperature control system, a second aeration device and at least one photobioreactor according to claim 1, wherein the at least one photobioreactor is connected with the second aeration device via a gas-liquid heat exchanger immersed in a thermal-insulation water tank.

11. The algae cultivation system according to claim 10, wherein the aeration pipe temperature control system comprises a thermal-insulation water tank, a hot water generation unit, a cold water supply unit, a gas-liquid heat exchanger and a controller, the cold water supply unit, the hot water generation unit and the thermal-insulation water tank are sequentially connected; the gas-liquid heat exchanger is immersed in the thermal-insulation water tank, and has one end thereof connected with the second aeration device and the other end connected with the photobioreactor; the controller is connected with the cold water supply unit and the hot water generation unit to control cold water supply of the cold water supply unit and hot water generation of the hot water generation unit.

12. The algae cultivation system according to claim 11, wherein the hot water generating unit is a solar water heater, the installation position of the solar water heater is higher than that of the thermal-insulation water tank; a microporous gas disperser is provided at the bottom of the photobioreactor, the gas-liquid heat exchanger is connected with the microporous gas disperser.

13. The algae cultivation system according to claim 11, wherein the cold water supply unit comprises a cold water source and a cold water pump, the cold water source is connected with the solar water heater through the cold water pump, and the cold water pump is connected with the controller.

14. The algae cultivation system according to claim 11, wherein a temperature sensor is arranged in the thermal-insulation water tank, and the temperature sensor is connected with the controller.

15. The algae cultivation system according to claim 13, wherein the cold water source is a cold water tank, the thermal-insulation water tank and the cold water tank are arranged in a shape of rectangular ambulatory-plane with the cold water tank located outside the thermal-insulation water tank, the height of the cold water tank is lower than the height of the thermal-insulation water tank, and the top of the thermal-insulation water tank is provided with an overflow channel which connects the thermal-insulation water tank and the cold water tank.

16. The algae cultivation system according to claim 11, wherein the second aeration device comprises a wind-driven compressor and a compressed gas storage tank connected with each other, wherein the compressed gas storage tank is connected with the gas-liquid heat exchanger.

17. The algae cultivation system according to claim 11, further comprising a liquid inlet pipe network and a liquid outlet pipe network, wherein the at least one photobioreactor comprises a plurality of photobioreactors, the liquid inlet of each photobioreactor is connected with the liquid inlet pipe network, and the liquid outlet of each photobioreactor is connected with the liquid outlet pipe network.

* * * * *